United States Patent [19]

Ericson

[11] 4,303,065
[45] Dec. 1, 1981

[54] ORTHOPEDIC APPLIANCE

[76] Inventor: Albert L. Ericson, 2309 E. Hawthorne St., Tucson, Ariz. 85719

[21] Appl. No.: 114,578

[22] Filed: Jan. 23, 1980

[51] Int. Cl.³ .............................................. A61F 3/00
[52] U.S. Cl. ................................................. 128/80 A
[58] Field of Search ........................... 128/80 A, 87 C

[56] References Cited
U.S. PATENT DOCUMENTS

| | | | |
|---|---|---|---|
| 2,482,646 | 9/1949 | Brachman et al. | 128/80 A |
| 2,514,870 | 7/1950 | Israel | 128/80 A |
| 2,963,020 | 12/1960 | Moran | 128/80 A |
| 4,040,416 | 8/1977 | Zentman | 128/80 A |

Primary Examiner—John D. Yasko
Attorney, Agent, or Firm—Frank P. Cyr

[57] ABSTRACT

An orthopedic appliance adapted to be employed as a means for correcting a deformity in a child's feet particularly where the feet are turned inwardly towards each other commonly referred to as pigeontoed. The appliance comprises essentially of a pair of flat plates to which the child's shoes are secured, with hinge members mounted on each of said flat plates and a pair of link bars secured to each of the aforesaid hinge members to thereby enable the user of the appliance to move one foot relative to the other foot while still maintaining the angle of one foot in a set position relative to the angle of the other foot.

5 Claims, 2 Drawing Figures

ORTHOPEDIC APPLIANCE

BACKGROUND OF THE INVENTION

A number of orthopedic appliances have been devised in the past to correct foot deformities in young children, the deformities usually being in that the feet are directed inwardly towards one another, this deformity is commonly referred to as pigeon-toed. These prior devices for the most part were usually employed during the sleeping periods of the child since these prior devices rendered the child's feet almost if not completely immobile.

With the above in mind, it is one object of the invention to so structure an orthopedic device adapted to correct foot deformities such as a so called pigeon-toed condition of the feet which can be adapted to the feet of the child and which will permit a limited amount of mobility for the child whenever the appliance is employed to cure the aforesaid feet deformity.

Another object of the invention is to so structure an orthopedic appliance for correcting a deformity in the feet of a child which, when applied to the feet of the child, will not impede the natural movement of the feet when the child is crawling or when the child assumes a standing or walking position.

Another object of the invention is to provide a pair of sole plates for the orthopedic appliance which will permit for the attachment thereto of a pair of the child's shoes and when so secured thereto, the outward angle of the disposition of the shoes may be varied and subsequently set in the desired outward angle of disposition of the shoes so as to maintain the child's feet at a desired outward angle with respect to one another so as to correct the inward pointing of the feet commonly referred to as pigeon-toed.

Another object of the invention is to hingedly mount a pair of sole plates to a linkage arrangement between the aforesaid pair of sole plates which will permit the user of the applicant to elevate one foot with respect to the other foot and likewise permit one foot to be moved forward when elevated as in a walking movement. The hinge-linkage arrangement, aforesaid, will also permit the user of the appliance to advance one foot forwardly and/or rearwardly with respect to the other foot such as is experienced when a child crawls.

Further objects, features and advantages of the present invention will be more fully appreciated by reference to the following detailed description of a presently preferred, but nonetheless illustrative embodiment in accordance with the present invention when taken in conjunction with the accompanying drawing, wherein:

DESCRIPTION OF THE PREFERRED EMBODIMENTS

Figure 1:
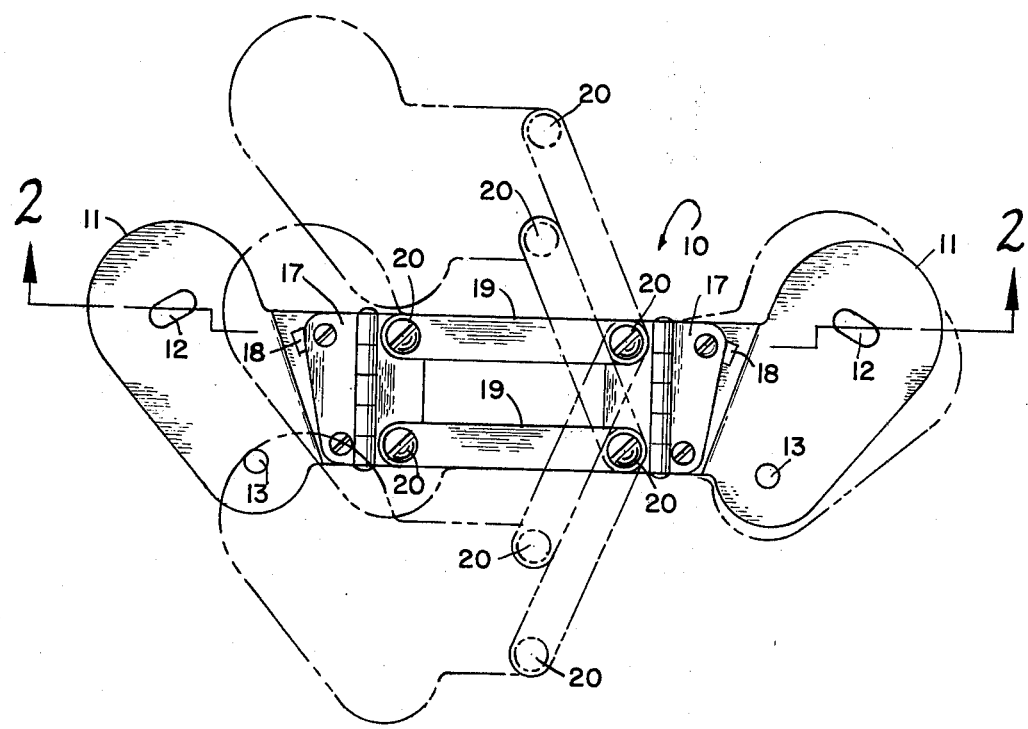
FIG. 1 is a top plan view of the orthopedic appliance of the present invention with phantom lines indicating the various positions of the foot attainable by the user of the appliance; and, FIG. 2 is a section taken on lines 2—2 of FIG. 1 looking in the direction of the arrows.

Referring now to the drawings, the orthopedic appliance of the present invention is shown generally by reference numeral 10. Like reference numerals will be employed throughout the description of the invention to designate like parts throughout the several views shown in the drawings. Essentially, the appliance comprises a pair of sole plates 11 preferably made of aluminum so as to reduce the weight of the appliance. The sole plates are each provided with openings 12 and 13 through which extend fastener means 14 of any known construction such as screws or the like. The shoes 15 are secured to the aforesaid sole plates 11 by means of the fastener means 14.

Referring more particularly to FIG. 1 of the drawings, it will be noted that openings 12, which are provided at the toe end of the plates, are in the nature of elongated slots for a purpose to be explained more fully hereinafter.

Secured to the sole plates in any known manner as by rivets or screws 16 are steel hinge plates 17 and it will be noted that the toe ends of the hinge plates are each provided with slots 18 which are formed in the sole plates 11, again for a purpose to be described more fully hereinafter.

Pivotally secured to the hinge plates are a pair of parallel bars 19 and any known means for pivotally securing the bars to the hinge plates may be employed for securing the parts together. Shown in the drawings are screws 20 employed for pivotally securing the bars to the hinge plates 17. However, as stated previously, any fastener means may be employed for pivotally securing the bars to the said hinge plates. Rubber soles 21 may be secured in any known manner to the undersurface of the sole plates to provide traction with the floor.

Having thus described the structure of the orthopedic appliance, I will now describe the manner of use thereof.

The shoes of the child are secured to the sole plates with the heel portion of the shoe secured to the sole plates by extending a suitable fastener means through openings 13 provided in the sole plates. The toe portion of the shoe is secured to the sole plates by extending a suitable fastener means through the slot-like openings 12. The slots 12 will permit the shoes to be adjustably secured to the aforesaid sole plates. In lieu of the slots 12, a plurality of spaced openings may be provided in the sole plates so as to provide a means for adjustably securing the shoes to the sole plates. The angle of disposition of the shoes when secured to the sole plates may be varied. The aforesaid slots 12 or the aforesaid spaced openings in the sole plates will permit for the adjustment of the shoes on the sole plates. Once the shoes have been secured to the sole plates and the same extend in the desired angle, suitable fastener means are employed for securing the shoes in their desired angle. While the phantom lines for the right sole plate 11 are shown in the drawings, it will be understood a like adjustment of the angle of the left sole plate will be made possible in the manner described. A further adjustment of the angle of disposition of the sole plates, as shown in phantom lines for the right shoe as shown in FIG. 1 of the drawings, is achieved by reason of the slots 18 which are formed in the sole plates and when the angle of disposition of the sole plates has been determined, the same may be securely locked in their adjusted position by means of a suitable fastener extending through the hinge plates and the said slots. Thus, the shoes may be secured to the sole plates and extended in the desired angle of disposition relative to one another and also, the angle of disposition of the sole plates may be adjusted so that through the aforesaid means of adjustment, the shoes will be caused to extend in the desired direction to thus effect a correction of the pigeon-toed condition of the user of the appliance.

Figure 2:
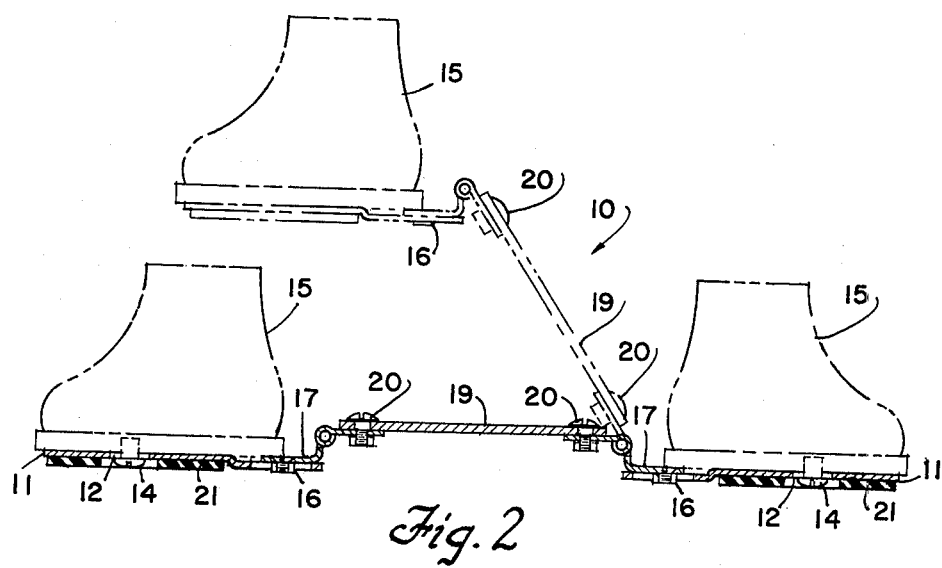

As stated previously, the appliance may be employed to correct a pigeon-toed condition of an infant still in the crawling stage or when the infant has reached the walking stage. During the crawling stage, the parallely arranged bars will permit for the feet of the wearer of the appliance to advance one foot with respect to the other such as shown in phantom lines in FIG. 1 of the drawings, and during the walking stage, one foot may be elevated with respect to the other foot such as shown in FIG. 2 of the drawings and when so elevated the same may be advanced with respect to the other foot again, by reason of the linkage and pivotal connections described above.

It will be apparent from the above description of a preferred embodiment of the invention that the particular size of the sole plates and length of the parallel bars will be dictated by the size and strength of the patient to be treated. As the child grows in size, larger shoes may be readily adapted to the same orthopedic appliance. Further, as treatment decreases the extent of the deformity, the relative angular displacement of the sole plates may be changed readily and conveniently at home to adjust the appliance to the child's changing orthopedic needs.

Having fully described my invention, it is to be understood that I do not wish to be limited to the details set forth, but rather the scope of the invention is to be set forth in the appended claims.

I claim:

1. An orthopedic appliance adapted for attachment to the shoes of a child comprising a pair of sole plate members, openings formed in the ball and heel portions of the sole plate member, hinge members mounted directly on the undersurface of said sole plate members, elongated openings formed along one side of said sole plate members, a fastener extending through said elongated elongated openings and said hinge members, a parallel linkage pivotally secured to said hinge members, the openings formed in the ball portion of the plate members providing a means for adjustably securing the shoes to the sole plate members and the elongated openings formed in said sole plate members providing a means for adjustably securing said sole plates to said hinge plates.

2. The structure recited in claim 1 wherein said linkage comprises a pair of parallely disposed parallel bars.

3. The structure recited in claim 1 wherein said hinge means are provided with adjustment slots formed therein whereby said sole plates may be adjustably secured to said hinge means.

4. The structure recited in claim 1 wherein a slot is provided in said sole plate to thereby permit for the adjustment of the angle of disposition of the shoe secured thereto.

5. The structure recited in claim 2 wherein each end of the parallel bars are pivotally mounted to said hinge means.

* * * * *